United States Patent [19]
Schlipalius

[11] Patent Number: 5,705,180
[45] Date of Patent: Jan. 6, 1998

[54] THERAPEUTIC AGENT FOR THE TREATMENT OF MELANOMAS

[75] Inventor: Lance Elliott Schlipalius, Ashwood, Australia

[73] Assignee: Betatene Limited, Cheltenham, Australia

[21] Appl. No.: 525,665

[22] PCT Filed: Mar. 22, 1994

[86] PCT No.: PCT/AU94/00141
§ 371 Date: Sep. 22, 1995
§ 102(e) Date: Sep. 22, 1995

[87] PCT Pub. No.: WO94/21231
PCT Pub. Date: Sep. 29, 1994

[30] Foreign Application Priority Data
Mar. 22, 1993 [AU] Australia .................. PL7934

[51] Int. Cl.$^6$ .................................................. A61F 2/02
[52] U.S. Cl. ........................................................ 424/423
[58] Field of Search .................................................. 424/423

[56] References Cited

U.S. PATENT DOCUMENTS 5,079,016  1/1992  Tood, Jr. .................... 426/250

FOREIGN PATENT DOCUMENTS 0494654  7/1992  European Pat. Off. .
9205780  4/1992  WIPO .

*Primary Examiner*—Carlos A. Azpuru
*Attorney, Agent, or Firm*—Burns, Doane, Swecker & Mathis, L.L.P.

[57] ABSTRACT

The present invention provides a therapeutic agent for the treatment of a melanoma or melanomas by injection or intravenously including a mixture of: (a) a water soluble dispersible component; (b) an emulsifier component; and (c) a water insoluble carotenoid component in a suitable carrier medium.

27 Claims, 3 Drawing Sheets

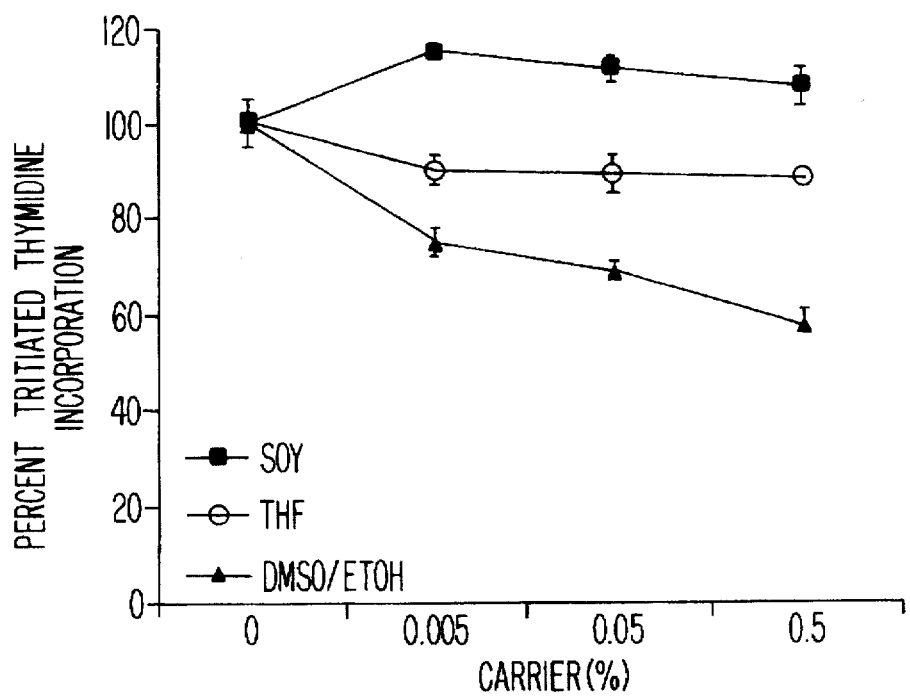
FIG. IA
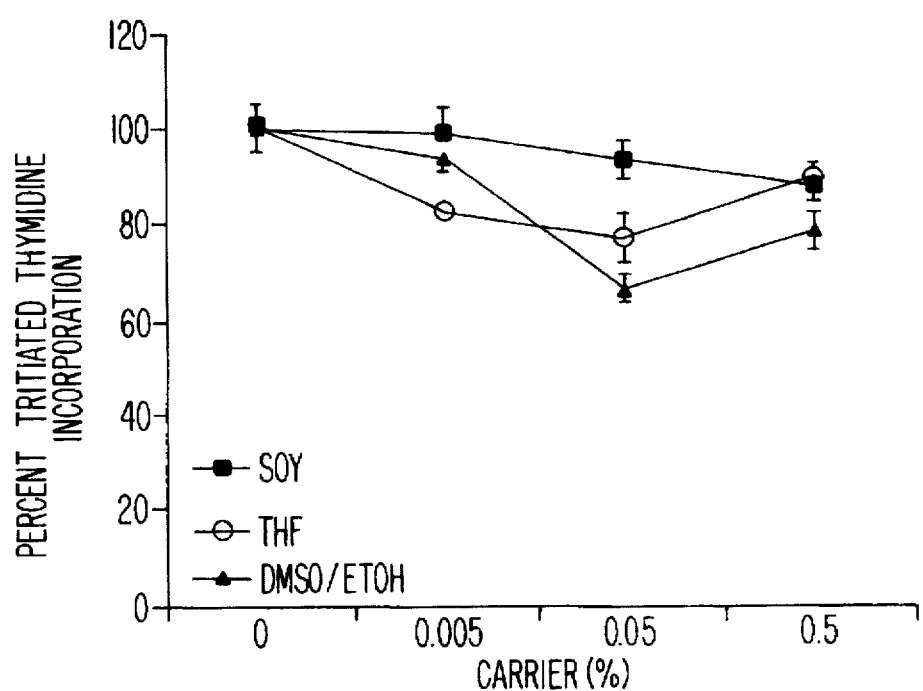
FIG. IB

THERAPEUTIC AGENT FOR THE TREATMENT OF MELANOMAS

FIELD OF THE INVENTION

The invention relates to a therapeutic agent for the treatment of a melanoma or melanomas and a method for such treatment.

BACKGROUND OF THE INVENTION

Melanomas are caused generally by the exposure of skin to sunlight. Persons of fair complexion have the greatest risk especially those who develop moles.

Melanomas originate from a change in normal skin cells, melanocytes, which produce the brown pigment melanin we recognise as tan. Moles and freckles result from areas of the skin with many melanocytes.

The influence of light on melanocytes is one way by which they can be changed to grow and divide differently, possibly causing a melanoma. The melanomas may be malignant, spreading to other parts of the body. Melanomas which do not spread are called benign.

Although melanomas normally form on exposed skin they can start in places such as the mouth or bowel.

Melanomas grow in size and need to be surgically removed before they spread and invade other parts of the body. If the melanomas spread to the inner organs, removal and treatment is more difficult and chemotherapy or radiotherapy need to be employed.

It has been hypothesised that carotenoids and in particular beta-carotene may reduce the risk of breast, lung, colon, prostate and cervical cancer, heart disease and stroke and may retard macular degeneration. In this respect, one hypothesis is that in mammals beta-carotene is converted to vitamin A and vitamin A analogues or retinoids (see Moon RC: Comparative aspects of carotenoids and retinoids as chemopreventive agents for cancer. J Nutr 119:127-134, 1989). It is this pro-vitamin A activity and the ability to prevent oxidative damage that has made carotenoids and in particular beta-carotene a compound of interest in chemopreventive studies. For instance, anti-oxidants are used, amongst other things, to quench free radicals that are by-products of normal metabolism in cells.

Beta-carotene has also been used in the treatment of erythropoietic protoporphyria (EPP). EPP is a genetic disease causing an inadequacy in the metabolism of porphyrin compounds. It results in a rapid blistering of the skin on exposure to sunlight.

When considering the use of carotenoid compositions for human application an immediate difficulty arises as a result of the nature of carotenoids.

Carotenoids are lipophyllic and therefore not soluble in water in useful quantities. It is believed that they are transported in the bloodstream as low density lipoproteins.

The current principal means by which carotenoids are introduced into the body is orally. However, this method is often unsatisfactory because the poor absorption of the carotenoid composition by the alimentary canal limits the concentrations in the blood which can be achieved. Further, there will be a substantial delay before a required level of carotenoids in the bloodstream or a specific organ is reached. Sometimes the required level cannot be reached as certain individuals do not absorb carotenoids very well, especially beta-carotene. There is about a tenfold difference in the ability of human individuals to absorb ben-carotene. There have been over 500 carotenoids isolated, but only approximately 15 have been shown to occur in the bloodstream.

Physicians often seek to administer compounds by injection or by intravenous drip rather than oral ingestion. However, because of the virtual water insolubility of carotenoid compositions it is very difficult to administer them either by injection or intravenously. The compound must be made dispersible in an aqueous base so that it is available to the body's cells. In this regard, the base must be compatible with, for example, the bloodstream or lymph, and the material must be prepared in a biologically sterile form. The base must itself be non-toxic to the human cells.

To date several in vitro studies have taken place to determine the effect of beta-carotene on normal and transformed cell types using solvents to solubilise the beta-carotene such as tetrahydrofuran, butanol, chloroform, hexane, dimethylsulfoxide, ethanol or in a liposome micelle. Previous liposome preparations have shown toxicity in cell line cultures as well as being limited in application (see Bertram J S, Pung A, Churley M, et al: Diverse carotenoids protect against chemically induced neoplastic transformation. Carcinogenesis 12:671-678, 1991; Hazuka M B, Prasad-Edwards J, Newman F, et al: Beta-carotene induces morphological differentiation and decreases adenylate cyclase activity in melanoma cells in culture. J Am Coll Nutr 9:143-149, 1990; Schultz T D, Chew B P, Seaman W R, et al: Inhibitory effect of conjugated dienoic derivatives of linoleic acid and beta-carotene on the in vitro growth of human cancer cells. Canc Letters 63:125-133, 1992; Schwartz J L, Shklar G: The selective cytotoxic effect of carotenoids and a-tocopherol on human cancer cell lines in vitro. J Oral Maxillofac Surg 50:367-373, 1992; Schwartz J L, Tanaka J, Khandekar V, et al: Beta-Carotene and/or Vitamin E as modulators of alkylating agents in SCC-25 human squamous carcinoma cells. Canc Chemother Pharmacol 29:207-213, 1992; Zhang L-X, Cooney R V, Bertram J S: Carotenoids enhance gap junctional communication and inhibit lipid peroxidation in C3H/10T1/2 cells: relationship to their cancer chemopreventive action. Carcinogenesis 12:2109-2114, 1991; and Zhang L-X, Cooney R V, Bertram J S: Carotenoids up-regulate connexin 43 gene expression independent of their provitamin A or antioxidant properties. Canc Res 52:5707-5712, 1992). These solvents have been found to have a toxic effect which is dose dependent. These solvents are also incompatible with human blood or lymph for the purposes of intravenous or injectable preparations.

Accordingly, investigations were carried out to develop a carotenoid composition which could be accepted by the human body and other animals and display efficacy in the treatment of melanomas.

DESCRIPTION OF THE INVENTION

In one embodiment of the invention a therapeutic agent is provided for the treatment of a melanoma or melanomas including a mixture of:

(a) a water soluble or dispersible component;
(b) an emulsifier component; and
(c) a water insoluble carotenoid component in a suitable carrier medium.

Preferably, the water soluble or dispensible component is in the range of 30% to 90% by weight.

In a further preferred form of the invention, the water soluble or dispersible component is selected from sugar alcohols, sugars, amino acids, water, vitamins, blood serum or plasma, lymph, buffers and combinations and polymers of these materials, and injectables that are well known in the industry such as mineral salt preparations and dextrose solutions or combinations of these components.

More preferably, the sugar alcohol is glycerol and in yet a further preferred embodiment, glycerol is in the range of 30% to 90% by weight.

In yet a further preferred form of the invention, the emulsifier component is in the range of 0.2% to 20% by weight and more preferably 1.0% to 10% by weight.

In yet another further preferred embodiment of the invention, the emulsifier component is selected from glycerides (including preferably monoglyceride and diglyceride structures from plant and animal sources), polyglycerol esters, lecithins and other phospholipids. More preferably the glyceride is glyceryl mono-oleate.

In another preferred form of the invention, the water insoluble carotenoid component is beta carotene. In yet a further preferred form that water insoluble carotenoid component comprises a predominantly 2% to 50% by weight beta-carotene in soya bean oil composition. More preferably, the beta carotene concentration is a predominantly 20% to 40% by weight and most preferably predominantly 30% by weight.

Preferably, the beta-carotene is a mixture of cis beta-carotene and all trans beta-carotene. Typically, the cis beta-carotene content of the beta-carotene is in the range of 50% and 90%, more preferably 70% and 85%. More preferably, the beta-carotene is predominantly 9 cis beta-carotene in a preferred range of 60% to 90%. In an even more preferred embodiment, the active carotenoid component of the composition is in the range of 0.1% to 10% by weight and more preferably 1% to 5% by weight.

In yet a further preferred form of the invention, the carrier medium used to carry the water insoluble carotenoid component is selected from the group comprising fatty acids and triglyceride lipids and non-saponifiable lipid preparations, certain suitable petroleum hydrocarbons including octadecane and combinations of the foregoing compounds.

In yet a further preferred form of the invention, the triglyceride lipids are selected from the group comprising fats and/or oils derived from plant sources such as seed oils including soya bean, cotton seed and sunflower and from animal sources including fish and beef. More preferably, the carrier medium is in the range of 0.1% to 40% by weight and even more preferably 1% to 20%.

In a preferred form of the invention, the agent is diluted for direct introduction into the bloodstream or melanoma or melanomas and more preferably, the diluting solution is selected from aqueous buffers, normal intravenous preparations (including isotonic saline or 5% dextrose solution) and blood serum and combinations of the foregoing for administration to cells in vivo and cell line culture media for administration to cells in vitro.

In a further form of the invention, a method of treatment of a melanoma or melanomas is provided including the step of introducing directly into the bloodstream or melanoma or melanomas, an effective amount of a therapeutic agent as described above. Preferably, the effective amount is from 0.1 to 10.0 micrograms/ml and more preferably, 0.3 to 3.0 micrograms/ml of the therapeutic agent contacting the melanoma cells.

More preferably, the therapeutic agent is directly introduced into the bloodstream by injection or intravenously. Even more preferably, the therapeutic agent is injected directly into the site of the melanoma or melanomas.

The term "mixture" as used herein is intended to include various physical forms including emulsions, solutions and crystal suspensions.

BRIEF DESCRIPTION OF THE DRAWINGS

FIG. 1 are graphs showing the effect of carriers on DNA synthesis in human metastatic melanoma and neonatal melanocytes. In summary, the melanoma cell strain, c81-46a and melanocytes were incubated for 72 hours with soybean oil extract, tetrahydrofuran and a 3:1 mixture of dimethylsulfoxide:ethanol. Each data point is the mean of 6 wells +/− percent standard error as compared to control.

FIGS. 1, 2 and 4 refer to "Percent Tritiated Thymidine Incorporation" which is a measure of DNA synthesis activity.

EXAMPLES

Figure 2:
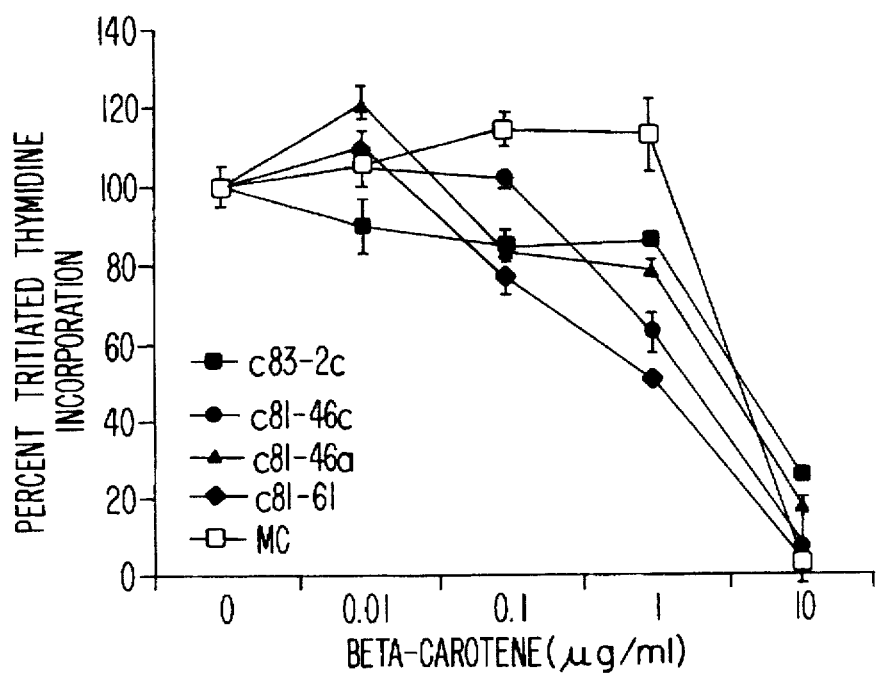
FIG. 2 is a graph showing the effect of beta-carotene on DNA synthesis in human metastatic melanoma and neonatal melanocytes. In summary, melanoma cell strains: c83-2c, c81-46c, c81-46a, c81-61 and melanocytes (MC) were incubated for 72 hours with ben-carotene. Each data point is the mean of 6 wells +/− percent standard error as compared to control. Diluent (soy) concentration=0.05%.

The following examples demonstrate the effectiveness of carotenoid compositions in the treatment of melanomas and the relative non-toxicity of these compositions.

Details of the experiments conducted in relation to the invention are as follows.

Materials (a) Cell Cultures

The method used to isolate and culture melanocytes is a combination of the procedures developed by Eisinger and Marko (see Eisinger M. Marko O: Selective proliferation of normal human melanocytes in vitro in the presence of phorbol ester and cholera toxin. Proc Natl Acad Sci 79:2018–2022, 1982) and Halaban and Alfano (see Halaban R. Alfano FD: Selective elimination of fibroblasts from cultures of normal human melanocytes. In Vitro 20:45–47, 1984).

Briefly, foreskin samples were collected from newborn infants, and the melanocytes isolated and transferred to a T-75 flask. Primary neonatal melanocytes were cultivated in MCDB 153 medium (Irvine Sci.) as described by Halaban (see Halaban R, Ghosh S, Baird A: bFGF is the putative natural growth factor for normal human melanocytes. In Vitro Cell Develop Biol 23:47–52, 1987) and modified by Kath (see Kath R, Rodecsk U, Menssen H D et al: Tumor progression in the human melanocytic system: Anticancer Res 9:865–872, 1987). Fibroblast contamination was suppressed by adding geneticin (250 micrograms/ml) to the medium for 2 days. Melanoma cell strains (c81-46a, c81-46c, c81-61, c83-2c) were cultured in F-10 (Fisher sci.) with 5% fetal calf serum, 5% newborn calf serum (Gemini Sci.), penicillin (100 units/ml) and streptomycin (0.1 milligrams/ml) (Sigma). The passage number for the melanoma cell strains used was less than 8, and the melanocytes was less than 5. The melanoma cell strains have previously been characterised (see Bregman M D, Meyskens F L: Inhibition of human malignant melanoma colony-forming cells in vitro by prostaglandin Al, Canc Res 43:1642–1645, 1983; Thomson S P, Meyskens F L: Methods of measurement of self-renewal capacity of clonogenic cells from biopsies of metastatic human malignant melanoma. Canc Res 42:4606–4613, 1982; and Yohem K H, Slymen D J, Bregman M D, et al: Radiation survival of murine and human melanoma cells utilizing two assay systems; monolayer and soft agar. Br J Canc 57:64–69, 1987). A number of other tumour cell lines were also tested namely, A-431 (a human epidermoid carcinoma), WiDr (a human colon adenocarcinoma). WI-38 (normal human fetal lung fibroblasts) (all obtained from the American Type Culture Collection) and Lu-CSF-1 (a human lung adenocarcinoma) (provided by the University of California at Irvine). These four cell lines were cultured in DMEM medium (Fisher Sci.), 5% fetal calf serum, 5% newborn calf serum, penicillin (100 units/ml) and streptomycin (0.1 milligrams/ml).

(b) Chemicals

The beta-carotene was isolated from the alga Dunaliella salina and represented 85–90% of the total carotenoids, with half of the balance consisting of oxycarotenoids (lutein and zeaxanthin) and the remaining half of alpha-carotene. Gamma-carotene is normally undetectable as characterised by high pressure liquid chromatography. The soya bean oil was isolated from soya beans. A crystalline suspension of beta-carotene and soya bean oil was created. This resultant phase was then emulsified into the composition described. It was then sterilised by heat or filtration. Prior to testing on the cell lines each vial of the composition was sub-aliquoted into cryogenic vials (Costar) with a fresh vial used for each experiment. Throughout all procedures, beta-carotene was protected from direct light.

Tetrahydrofuran and ethanol (Fisher Sci.) of the highest quality available was used. Dimethylsulfoxide was purchased from Sigma.

The details of the emulsified beta-carotene composition are as follows:

| | | % by weight |
|---|---|---|
| (i) and | Beta-carotene | 2.4% |
| (ii) | SOY being: | |
| | Soya bean oil | 6.8% |
| | Glyceryl mono-oleate | 7.2% |
| | Glycerol | 66.7% |
| | Water | 16.9% |

The above composition can be prepared by the following method. A crystalline suspension of beta-carotene in soya bean oil is heated and glyceryl mono-oleate is added. This oil phase is dispersed in the glycerol-water phase by high shear mixing followed by homogenisation at 60°–70° C. Typically, a homogenisation pressure of 8,000 to 10,000 PSI is used, however, this pressure will vary according to the machine that is used. The resulting product is then sterilized by heat processing. Typically, heat processing is effected by autoclaving at 121° C. for 15 minutes in a pack for dispensing (3ml glass vial). Optionally, 0.3% of the anti-oxidant tocopherols is added to overcome any toxicity that may develop over a period of time.

(c) Experimental Conditions

Incorporation of tritiated thymidine into DNA was measured in the following manner. Cells were seeded into a 96 well plate (Falcon) and allowed to grow to 50% confluency (24 hours) after which fresh medium alone, fresh medium with beta-carotene or fresh medium with a carrier (carrier concentration=0.05%) were added and incubated for 72 hours. DNA synthesis was measured by labelling with [methyl-3H]-thymidine (2.5 uCi/ml. 20 Ci/mmol Dupont-New England Nuclear) added to the medium during the last 15 hours of the treatment period. After incubation, cells were harvested using a PhD cell harvester (Cambridge Research Inc.). Radioactivity incorporated was determined by liquid scintillation counting (LS5000TD, Beckman Instruments) with an efficiency of 62.7%. The data is represented as percent tritiated thymidine incorporation as compared to control. Each data point is the mean of 6 wells +/− percent standard error.

Cellular proliferation was determined as follows. Cells were seeded into 6 well plates (Falcon) and allowed to grow to 50% confluency (24 hours). Fresh medium and the appropriate compound was added and cells then incubated for 72 hours. After incubation, cells were harvested with 0.25% trypsin and washed. Cells were counted on a Coulter Counter (Coulter Instruments) and viability determined by trypan blue exclusion. Each data point is the mean of 3 wells +/− percent standard error.

Results

To determine the effect of a number of carriers for beta-carotene on the activity of normal melanocytes and a metastatic melanoma cell strain, c81-46a thymidine incorporation was measured. Tetrahydrofuran ("THF"), a 3:1 mixture of dimethylsulfoxide/ethanol ("DMSO/ETOH") and the SOY were incubated with the cells for 72 hours at 0.005%, 0.05% and 0.5% concentration.

As shown in FIG. 1, the SOY did not effect incorporation of thymidine in the melanoma cells at any concentration of the diluent. THF had only a slight effect on the melanoma cells, while DMSO/ETOH decreased incorporation by 40% at the highest concentration.

FIG. 2 shows the effect of beta-carotene in the SOY carrier on normal melanocytes and four metastatic melanoma cell strains. At a concentration of 0.1 micrograms/ml, beta-carotene had a slight inhibitory effect on the melanoma cell growth. The most sensitive being c81-61 with a 20% decrease in DNA synthesis. However, the melanomas showed a differential response to beta-carotene at 1.0 micrograms/ml, ranging from no inhibition to greater than 40%. At the highest beta-carotene concentration (10 micrograms/ml), normal melanocytes and two of the melanomas (c81-61, c81-46c) were more than 95% inhibited. Although, c81-46a and c83-2c remained 20–25% unaffected.

Figure 3:
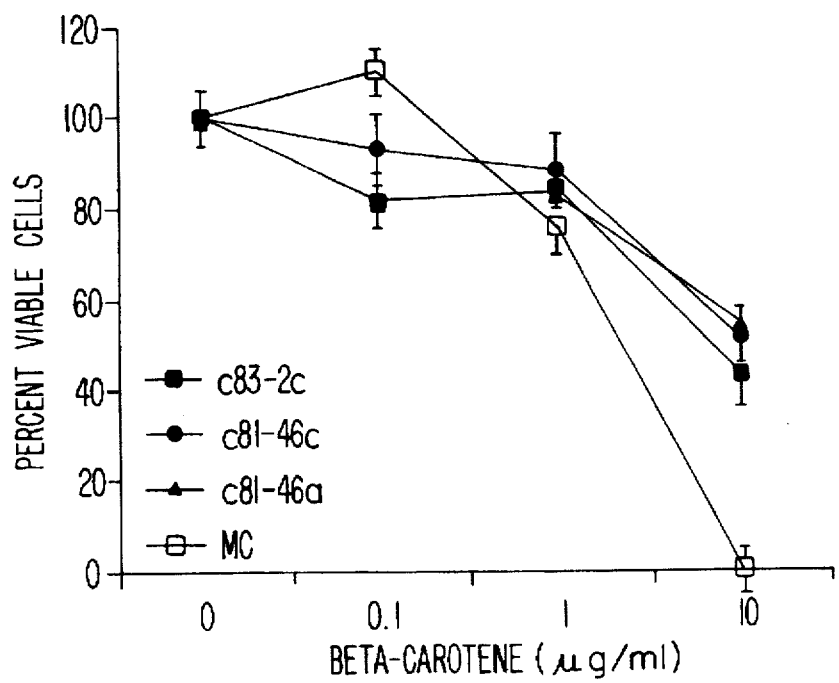
FIG. 3 is a graph showing the effect of ben-carotene on the proliferation of human metastatic melanoma and neonatal melanocytes. In summary, melanoma cell strains: c83-2c, c81-46c, c81-46a and melanocytes (MC) were incubated for 72 hours with beta-carotene and viability assessed by trypan blue exclusion. Each data point is the mean of 3 wells +/− percent standard error as compared to control. Diluent (soy) concentration=0.05%.

Additionally, viability, as measured by trypan blue exclusion, of normal melanocytes and the four metastatic melanomas was determined (FIG. 3). Beta-carotene at 1.0 micrograms/ml reduced viability by 20% while at 10 micrograms/ml no viable melanocytes were detected. Most striking is beta-carotene at the highest dose, which resulted in no viable melanocyte cells and 60% of the melanomas unaffected.

Figure 4:
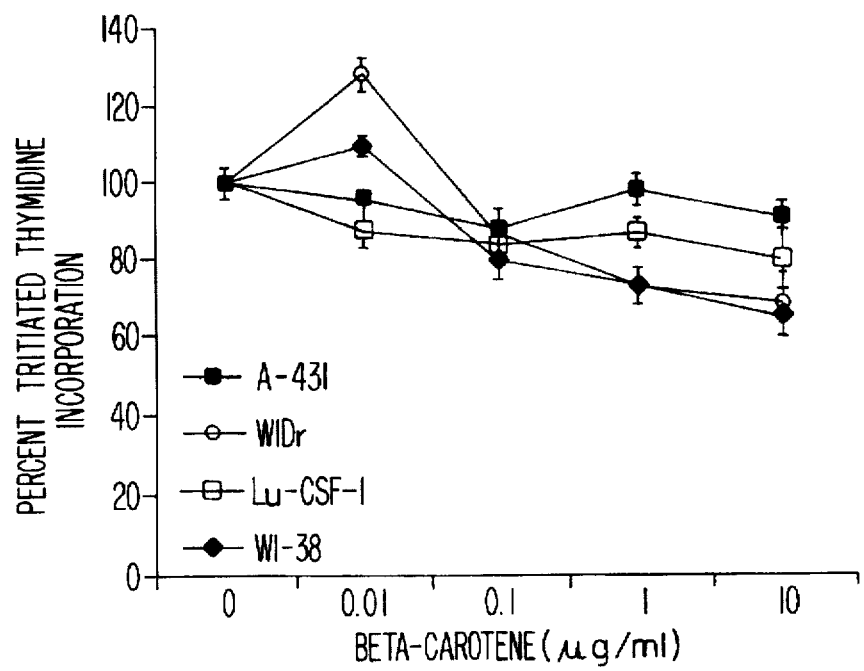
FIG. 4 is a graph showing the effect of beta-carotene on DNA synthesis in human tumor and normal cell lines. In summary, A431, epidermoid carcinoma; WiDr. colon adenocarcinoma; WI-38, fetal lung fibroblasts and Lu-CSF-1, lung adenocarcinoma were incubated for 72 hours with beta-carotene. Each data point is the mean of 6 wells +/− percent standard error as compared to control. Diluent (soy) concentration=0.05%.

The response of other tumor types was also assessed for their response to beta-carotene (FIG. 4). The human epidermoid carcinoma cell line, A-431, was unaffected by beta-carotene even at 10 micrograms/ml. The colon cell line, the normal lung fibroblasts and the lung adenocarcinoma cell line were minimally inhibited (10–20%).

Figure 5:
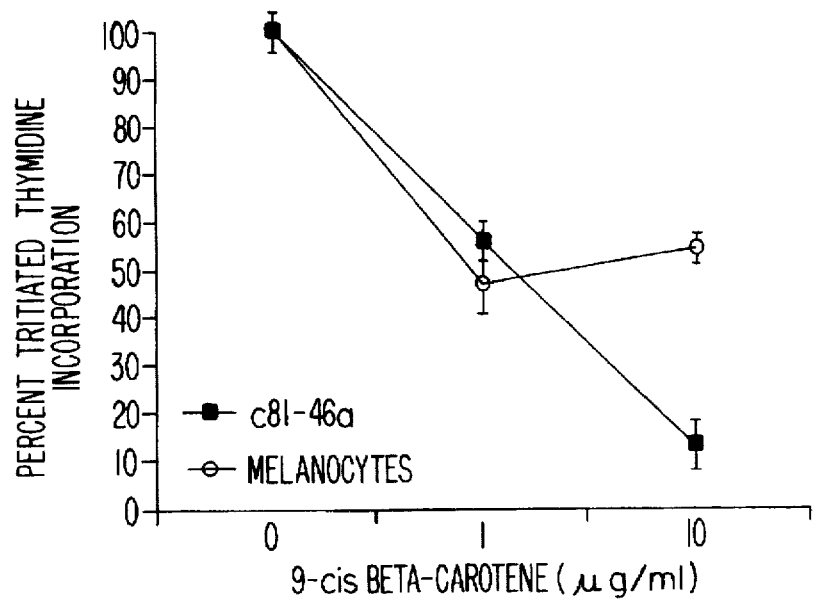
FIG. 5 is a graph showing the effect of 9-cis Beta Carotene on DNA synthesis in human metastatic melanoma and neonatal melanocytes. In summary, the melanoma cell strain c81-46a and melanocytes were incubated for 72 hours with 9-cis beta-carotene. Each data point is the mean of 6 wells +/− percent standard error as compared to control. Diluent (soy) concentration 0.05%.

FIG. 5 shows the effect of 9-cis beta carotene in the SOY carrier on normal melonocytes and one metastatic melonoma cell strain. At a concentration or 1.0 microgram/ml, both the normal melanocyte and the c81-46a were approximately 50% inhibited. At the higher concentration of 9-cis beta carotene (10.0 micrograms/ml), the metastatic melonoma cell strain was 90% inhibited while the melanocyte was slightly less inhibited than at 1.0 microgram/ml.

Without wishing to be limited to any specific theory, it appears that the mixture as illustrated in the above illustrations is a superfine emulsion.

In vitro studies to date have employed various chemical solvents as the carrier for beta-carotene. It has been found that the effect of these solvents alone is cytotoxic. The current testing as set out above has revealed that as measured by tritiated thymidine incorporation, the SOY did not effect the growth of normal human melanocytes or metastatic melanoma cell strains. However, solvents such as THF and a DMSO/ETOH mixture inhibited DNA synthesis in a concentration dependent manner.

As a novel carrier for beta-carotene, the SOY allowed the effect of beta-carotene to be measured without the confounding toxicity of a harsh solvent carrier that interferes with the response.

Melanocytes were selected as a human cell type which is sensitive to inhibition by a range of chemicals. The test results indicated that SOY did not inhibit incorporation of tritiated thymidine into the melanocyte DNA or the cell viability as determined by trypan blue exclusion.

Melanomas while typically not as sensitive to inhibition by a range of chemicals as melanocytes, were even more sensitive to even moderate levels of beta-carotene. This indicated a differential effect for melanomas.

I claim:

1. A method of treatment of a melanoma or melanomas including the step of introducing directly into the bloodstream or melanoma an effective amount of a therapeutic agent comprising a mixture of:
   (a) a sugar alcohol;
   (b) a glyceride; and
   (c) a therapeutically effective amount of a water insoluble carotenoid for treatment of melanoma or melanomas, in oil.

2. The method of treatment of a melanoma or melanomas according to claim 1, wherein the effective amount is from 0.1 to 10.0 micrograms/ml of the therapeutic agent contacting the melanoma cells.

3. The method of treatment of a melanoma or melanomas according to claim 1, wherein the effective amount is from 0.1 to 3.0 micrograms/ml of the therapeutic agent contacting the melanoma cells.

4. A method of treatment of a melanoma or melanomas according to claim 1, wherein the introduction of the therapeutic agent into the bloodstream is by injection or intravenously.

5. A method of treatment of a melanoma or melanomas according to claim 1, wherein the introduction of the therapeutic agent directly into the site of the melanoma or melanomas is by injection.

6. A therapeutic agent for the treatment of a melanoma or melanomas comprising a mixture of:
   (a) a sugar alcohol;
   (b) a glyceride; and
   (c) a therapeutically effective amount of a water insoluble carotenoid for treatment of a melanoma or melanomas, in oil.

7. A therapeutic agent according to claim 6 wherein the sugar alcohol is in the range of 30% to 90% by weight.

8. A therapeutic agent according to claim 6, wherein the sugar alcohol is glycerol.

9. A therapeutic agent according to claim 8, wherein the glycerol is in the range of 30% to 90% by weight.

10. A therapeutic agent according to claim 6, wherein the glyceride is in the range of 0.2% to 20% by weight.

11. A therapeutic agent according to claim 6, wherein the glyceride is in the range of 1.0% to 10% by weight.

12. A therapeutic agent according to claim 6, wherein the glyceride is glyceryl mono-oleate.

13. A therapeutic agent according to claim 6, wherein the water insoluble carotenoid component comprises beta-carotene.

14. A therapeutic agent according to claim 6, wherein the water insoluble carotenoid composition comprises 2% to 50% by weight beta-carotene in soya bean oil.

15. A therapeutic agent according to claim 6, wherein the water insoluble carotenoid composition comprises 20% to 40% by weight beta-carotene in soya bean oil.

16. A therapeutic agent according to claim 6, wherein the water insoluble carotenoid composition comprises 30% by weight beta-carotene in soya bean oil.

17. A therapeutic agent according to claim 16, wherein the beta-carotene comprises cis beta-carotene and all trans beta-carotene.

18. A therapeutic agent according to claim 17, wherein the beta carotene comprises 50% to 90% cis beta-carotene.

19. A therapeutic agent according to claim 17, wherein the beta-carotene comprises 70% to 85% cis beta carotene.

20. A therapeutic agent according to claim 17, wherein the cis beta-carotene comprises 9 cis beta-carotene.

21. A therapeutic agent according to claim 17, wherein the cis beta-carotene comprises 50% to 90% 9 cis beta-carotene.

22. A therapeutic agent according to claim 6, wherein the water insoluble carotenoid component of the composition is in the range of 0.1% to 10% by weight.

23. A therapeutic agent according to claim 6, wherein the water insoluble carotenoid composition is in the range of 1% to 5% by weight.

24. A therapeutic agent according to claim 6, wherein the vegetable oil is in the range of 1% to 40% by weight.

25. A therapeutic agent according to claim 6, wherein the carrier medium is in the range of 1% to 20% by weight.

26. A therapeutic agent according to claim 6, wherein the agent is diluted for direct introduction into the bloodstream or melanoma or melanomas of an effective amount of the composition.

27. A therapeutic agent according to claim 26, wherein the agent is diluted by aqueous buffers, normal intravenous preparations, blood serum, or combinations thereof.

* * * * *